United States Patent
Takakura et al.

(10) Patent No.: US 6,413,716 B1
(45) Date of Patent: *Jul. 2, 2002

(54) METHOD FOR DETECTION OF HUMAN PARVOVIRUS AND REAGENT THEREFOR

(75) Inventors: Fumihiro Takakura; Hiroyuki Sato; Yoshiaki Maeda, all of Chikushino (JP)

(73) Assignee: The Japanese Red Cross Society, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 219 days.

(21) Appl. No.: 08/665,377

(22) Filed: Jun. 18, 1996

(30) Foreign Application Priority Data

Jun. 26, 1995 (JP) ............................................. 7-159038

(51) Int. Cl.⁷ .......................... C12Q 1/70; G01N 35/00
(52) U.S. Cl. ...................... 435/5; 435/7.25; 435/40.5; 436/43; 436/51; 436/52
(58) Field of Search ........................ 435/5, 7.25, 40.5; 436/521, 43, 51, 52

(56) References Cited

FOREIGN PATENT DOCUMENTS

| JP | 64 000467 A | 11/1987 |
|---|---|---|
| JP | 1503675 | 12/1989 |
| JP | 488985 | 3/1992 |
| JP | 5504143 | 7/1993 |
| JP | 6293798 | 10/1994 |
| WO | WO8802026 | 3/1988 |
| WO | WO9013567 | 11/1990 |
| WO | WO9112269 | 8/1991 |
| WO | WO9410294 | 5/1994 |
| WO | WO94/22014 | 9/1994 |

OTHER PUBLICATIONS

Grunmeier et al., Annals of the New York Academy of Sciences, 130(2):809–818, Nov. 1965.*
Senda et al., Veterinary Microbiology, 12:1–6, 1986.*
Lennett, et al. ed., Diagnostic Procedures for Viral and Rickettsial Infections, 4th ed., American Public Health Assoc., pp. 205, 216–219, 227–229, 256–267, 415, 427–431, 457–458, and 469–475, 1969.*
Tokuhisa et al., "Hemagglutination of epizootic hemorrhagic disease virus", Archives of Virology, vol. 69, pp. 291–294, Medline abstract, 1981.*
Sato, et al., "Screening of Blood Donors for Human Parvovirus B19", The Lancet, vol. 346, pp. 1237–1238, Nov. 4, 1995.*
Hilfenhaus, et al., "Antibody Capture Hemadherence Tests for Parvovirus B19–Specific IgM and IgG," J. Virol Methods, vol. 45, pp. 27–37, 1993.*
Mathys, et al., "Hemagglutination with Formalin–Fixed Erythrocytes for Detection of Canine Parvovirus", Am J Vet Res, vol. 44, pp. 150–151, 1983.*
Chemical Abstracts, vol. 119, No. 21, Nov. 22, 1993, Columbus, Ohio, USA, K.E. Brown et al "Erythrocyte P antigen: Cellular receptor for B19 parvovirus", p. 793, No. 223 758e; & Science (Washington, D.C., 1883–) 1993, 262(5130), 114–17.
Chemical Abstracts, vol. 117, No. 15, Oct. 12, 1992, Columbus, Ohio, USA, K.E. Brown et al "Hemagglutination by parvovirus B19", p. 586, No. 148 318q; & J. Gen. Vivol. 1992, 73(8), 2147–9.
Chemical Abstracts, vol. 121, No. 15, Oct, 10, 1994, Columbus, Ohio, USA, R.C.N. Cubel et al. "Application to immunoglobulin M capture hemadherence asssays of hemagglutinationof monkey erythrocytes by native and recombinant human parvovirus B19 antigens", p. 836, No. 177 056r; & J. Clin. Microbiol. 1994, 32(8), 1997–9.
Chemical Abstracts, vol. 120, No. 11, Mar. 14, 1994, Columbus, Ohio, USA, S. Hilfenhaus et al. "Antibody capture hemadherence tests for parvovirus B19–specific IgM and IgG", pp. 759–760, No. 131 577u; & J. Virol. Methods 1993, 45(1), 27–37.
General Virology, vol. 73, p. 2147–2149, 1992.
Science, vol. 262, p. 114–117, 1993.

* cited by examiner

Primary Examiner—Brenda Brumback
(74) Attorney, Agent, or Firm—Christie, Parker & Hale, LLP

(57) ABSTRACT

A method for detection of human parvovirus B19, comprising the steps of: (1) bringing a sample into contact with fixed P-antigen positive red cells in a medium at pH 5.6±0.6; and (2) determining whether or not hemagglutination occurs; and a reagent for detecting human parvovirus B19, wherein the reagent comprises fixed P-antigen positive red cells.

1 Claim, 1 Drawing Sheet

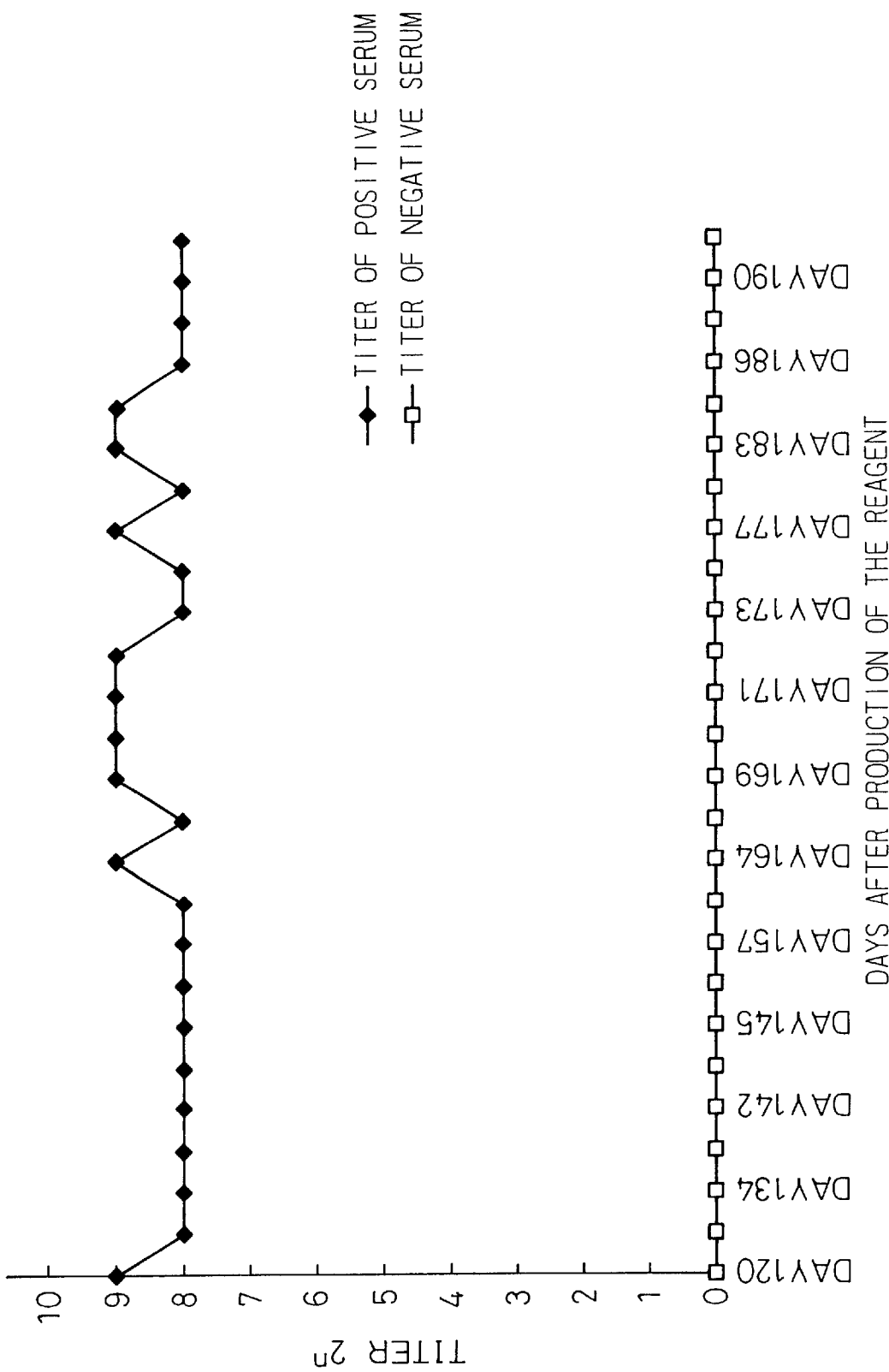

METHOD FOR DETECTION OF HUMAN PARVOVIRUS AND REAGENT THEREFOR

BACKGROUND OF INVENTION

1. Field of the Invention

The invention relates to a method for detecting human parvovirus B19, and reagents therefor.

2. Related Art

Human parvovirus B19 replicates in the nucleus of proliferating cells such as fetal liver cells and fetal cardiac myocytes. It is a non-enveloped virus and induces remarkable viremia in humans. It causes aplastic crisis in patients of chronic hemolytic anemia, erythema infectiosum, hydrops fetalis, febrile diseases, arthropathy, transient bone marrow failure and so on. B19 virus resists various inactivation procedures such as heat and detergent treatment.

B19 virus can be transmitted through blood, and it is important not to use infectious blood to prevent B19 virus infection by transfusion. There are two kinds of methods for detecting B19 virus infection, i.e., identification of the B19 virus itself and detection of IgM antibody specific to B19. The former methods include an indirect immunofluorescent (IF) method, a counter current immunoelectrophoresis (CIE) method, an enzyme-linked immunosorbent assay (ELISA) method, a radioimmunoassay (RIA) method, a dot blot hybridization method, and a polymerase chain reaction (PCR) assay. The latter includes the ELISA, RIA, and Western blotting methods.

The conventional methods require a long time and complicated manipulation and their sensitivity is not always sufficient. To date, B19 viremia could not be routinely checked on blood donations. Therefore, it is important to find a highly sensitive, quick and simple detection method for the B19 virus.

Brown K. E. et al have reported hemagglutination by human parvovirus B19 (Journal of General Virology, Vol. 73, p2147 to 2149, 1992). They also demonstrated that hemagglutination occurred via P-antigen (red cell membrane antigen) as a receptor for the B19 virus. (Science, Vol. 262, p114 to 117, 1993). However, while Brown et al indicate that the B19 virus causes agglutination of human red cells, they do not suggest that this phenomenon can be used for detecting the B19 virus.

The present invention provides a new method that is more sensitive and simple than previous methods.

SUMMARY OF THE INVENTION

To resolve the drawbacks in the conventional detection methods, the present inventors have realized a highly sensitive and reproducible method of detecting B19 virus using both fixed red blood cells and a buffer of pH 5.0 to 6.2.

Accordingly, the present invention provides a method for detection of human parvovirus B19 comprising the steps of bringing a sample into contact with fixed P-antigen positive red cells in a medium at pH 5.6±0.6, and determining whether or not hemagglutination occurs, and a reagent for said method.

BRIEF DESCRIPTION OF THE DRAWING

FIG. 1 shows the stability of the RHA reagent of the present invention.

PREFERRED EMBODIMENT FOR CARRYING OUT THE INVENTION

This invention relates to a new detection system for human parvovirus B19 and is characterized as follows. When fixed red cells having P-antigen and samples containing the virus are mixed together in a buffer of pH 5.0 to 6.2, hemagglutination occurs. The pH value positively influences the agglutination.

According to this invention, B19 viruses in a sample combine with P-antigen on the surface of red cells. Consequently, red cells bind to each other via the virus and hemagglutination occurs. By observing whether or not hemagglutination occurs, the present invention can determine the presence or absence of B19 virus in a sample. This method is 100 to 1,000 times more sensitive than the ELISA method.

The present invention uses O-group blood cells, with the P blood-group antigen, that are fixed with glutaraldehyde. Approximately 30% of the Japanese population are O-type as determined by ABO-blood typing. Almost all Japanese people are P-antigen positive, but very few Japanese are P-antigen negative (p-type). Therefore P-antigen positive blood must be confirmed by means of anti-P serum.

The present invention uses red cells fixed with glutaraldehyde. As to specific antigens, fixed red cells can remain in the same condition as untreated red cells for a long time. When using untreated cells, hemolysis occurs gradually within a few weeks, whereas fixed red cells keep the same condition for several years. Therefore using fixed cells, a stable result can be obtained. The fixation with glutaraldehyde should be done in 1% glutaraldehyde at 15 to 35° C. for 10 to 30 hours.

In the present invention, the fixed cells, as described above, and the samples are mixed together in a solution, containing a citrate-phosphate buffer or an acetate buffer, of pH 5.0 to 6.2. This buffer should preferably include a polymer, a protein, a sugar, sodium chloride, and a preservative.

The present methods uses polyvinylpyrrolidone and arabic gum as polymers. Polyvinylpyrrolidone enhances hemagglutination and arabic gum reduces non-specific reactions. Both of the polymers should be used at a concentration of 0.05 to 1.0%.

Seronegative human AB serum should be added to the buffer at a concentration of 0.1 to 2.0%, because serum protein reduces non-specific reactions. The addition of 0.5 to 3.0% sucrose in a buffer is preferable for long-term storage of fixed red cells.

The concentration of sodium chloride influences the detection sensitivity and the frequency of non-specific agglutination. The optimal concentration of sodium chloride is approximately 0.45 to 2.0%.

0.1 to 1.0% sodium azide may be added, as a preservative, to the buffer.

In this detection system, a blood sample is mixed with fixed red blood cells in a buffer as previously described. This assay can be done on a microplate at room temperature and a result can be obtained after 30 to 120 minutes. If a sample contains human parvovirus B19, hemagglutination occurs.

EXAMPLES

Next, the present invention is described in detail by means of Examples.

Example 1

Preparation of Red Cells

Red cells as a reagent for detecting B19 virus were prepared as follows.

Human O-blood cells with the P-antigen were washed more than three times with 1/15M phosphate buffered saline (PBS), pH 7.2. A 10% suspension of the red cells in PBS was fixed with glutaraldehyde at a final concentration of 1%. The fixed cells were washed twice with physiologic saline and once with PBS. The fixed red cells were suspended in PBS at a concentration of 25% and stored at 4° C.

Before the assay, the concentration of the fixed cells was adjusted in the suspension buffer to 1%. The suspension buffer is described as follows.

The suspension buffer consists of 0.1M citrate-phosphate buffer, at pH 5.6, containing 0.1% polyvinylpyrrolidone (PVP-K30), 0.1% arabic gum, 1% sodium chloride, 1% sucrose, and 0.1% sodium aside.

A sample dilution buffer was prepared by adding seronegative human AB serum, at a final concentration of 0.6%, to the suspension buffer.

Example 2

We compared this invention, a receptor-mediated hemagglutination (RHA) test, with a PCR test, an ELISA test, and a CIE test on twenty-one B19 virus positive samples.

(1) The Method of the Present Invention

Twenty-five μl of sample diluent buffer was added to a P6 microplate (OLYMPUS) from the first to the eighteenth well. Then we made two-fold serial dilutions of 25 μl of serum up to the eighteenth well. Twenty-five μl of 1% fixed red cell solution was added to each well and mixed together using a microplate mixer for 15 to 30 seconds. After 1 hour at room temperature, the results were obtained.

(2) ELISA

The diluted samples were added to the microwells coated with the IgM antibody specific to the B19 virus. After incubation and a washing procedure, a monoclonal-antibody specific to B19 was added to each well. After a washing step, peroxidase-conjugated anti-mouse IgG was added. Excess conjugate was removed by washing and the bound peroxidase was developed by adding the substrate. The intensity of the color is positively correlated with the concentration of B19 virus.

(3) Measurement of Copies of B19 (PCR)

At first, the detection limit in PCR was determined with plasmid containing B19 genome. A ten-fold dilution series of plasmid was amplified, and standard curve was obtained. Virus DNAs from ten-fold serial dilution of B19 viremic samples were obtained by a phenol-chloroform extraction method and used for PCR assay. The number of copies of the virus in sample serums were determined from the standard curve.

(4) CIE

At first, three-lined holes on agarose plates were made. Human parvovirus B19 antiserum was added to the plus terminal side, blood samples to central part, human parvovirus B19 positive serum to minus terminal side, and then the plates were electrophoresed in 30 mM barbiturate buffer (pH 8.6).

The result are indicated in table 1.

TABLE 1

Detection of 21 B19 positive samples in RHA, PCR, ELISA and CIE

| Sample-No. | Lot-No. | RHA titer | copies of the virus (/ml) | ELISA antigen | CIE antigen | CIE antibody |
|---|---|---|---|---|---|---|
| 194 | 086-0975 | 4096 | $4 \times 10^{10}$ | 1.581 | + | − |
| 195 | 471-6610 | 2048 | $4 \times 10^{10}$ | 0.907 | + | − |
| 196 | 090-0314 | 8192 | $4 \times 10^{11}$ | NT | + | − |
| 197 | 849-4973 | 8192 | $4 \times 10^{11}$ | 1.542 | + | − |
| 257 | 067-5238 | 8192 | $4 \times 10^{10}$ | 2.243 | + | − |
| 258 | 812-3182 | 4096 | $4 \times 10^{10}$ | 1.990 | + | − |
| 259 | 318-5775 | 8192 | $4 \times 10^{10}$ | 1.486 | + | − |
| 260 | 475-3114 | 2048 | $4 \times 10^{10}$ | 1.593 | + | − |
| 261 | 491-7509 | 1024 | $4 \times 10^{10}$ | 0.488 | + | − |
| 262 | 647-0846 | 8192 | $4 \times 10^{10}$ | 1.665 | + | − |
| 263 | 034-8953 | 8192 | $4 \times 10^{10}$ | 1.028 | + | − |
| 264 | 455-2829 | 8192 | $4 \times 10^{10}$ | 2.068 | + | − |
| 265 | 098-8479 | 8192 | $4 \times 10^{11}$ | 1.921 | + | − |
| 266 | 085-9943 | 8192 | $4 \times 10^{10}$ | 1.523 | + | − |
| 267 | 021-2032 | 4096 | $4 \times 10^{10}$ | 0.975 | + | − |
| 268 | 491-7184 | 8192 | $4 \times 10^{10}$ | 2.335 | + | − |
| 269 | 480-5296 | 4096 | $4 \times 10^{10}$ | 2.385 | + | − |
| 270 | 489-8200 | 8192 | $4 \times 10^{10}$ | 2.256 | + | − |
| 271 | 831-3167 | 2048 | $4 \times 10^{10}$ | 0.825 | + | − |
| 272 | 400-4427 | 4096 | $4 \times 10^{10}$ | 1.407 | + | − |
| 273 | 092-4293 | 512 | $4 \times 10^{10}$ | 0.623 | + | − |
| negative control | negative-1 | <2 | $<4 \times 10^{3*}$ | 0.076 | − | − |
| negative control | negative-2 | <2 | $<4 \times 10^{3*}$ | 0.083 | − | − |

NT: not tested
*: not detected by PCR using 2.5 μl of serum

As shown above, positive samples for ELISA and CIE were also positive for the RHA test. The detection limit of RHA is $10^5$–$10^6$ virus per ml. On the other hand, ELISA, CIE, and PCR can only detect more than $6.3 \times 10^7$ virus per ml, $3.6 \times 10^9$ virus per ml, and $4 \times 10^3$ virus per ml, respectively. These results suggest that RHA test is more sensitive than ELISA and CIE.

Example 3

We examined 27,265 samples including B19 positive serum by both methods, RHA and CIE. RHA test was applied to PK7200 (OLYMPUS, automated hemagglutination machine). Seventeen μl of sample serum were mixed with 250 μl of sample diluent buffer. Ten μl of the diluted sample was added, with 40 μl of 0.625% fixed red cells, to a P6 microplate. [Dilution rate; 1/39.25] The result of these samples was determined automatically after one hour.

This result indicates table 2.

TABLE 2

Comparison of RHA with CIE

| | | RHA | |
|---|---|---|---|
| | | (+) | (−) |
| CIE | (+) | 21 | 0 |
| | (−) | 19 | 27,225 |

Total sample number: 27,265

Twenty-one positive samples in CIE and RHA were also positive in PCR assay. Out of 19 samples, CIE(−) and RHA(+), 6 samples were positive in PCR. This observation suggests that RHA is more sensitive than CIE.

RHA rarely gives a false-positive reaction (13/27,265: 0.048%).

Example 4

From September to November in 1995, 211,701 donor samples were examined by RHA using PK7200. Positive samples in PK7200 were subjected to titration of RHA, RHA inhibition test shown below and PCR assay.

(1) RHA Inhibition Test for Confirmation

To confirm the positive reactions, inhibition of RHA was done by specific antibodies against B19 virus. Optimal concentration of B19 antibodies was determined by box titration.

In RHA inhibition test, two lines of microwells per sample in a P6 microplate were used. On one line, sample serum was serially diluted with sample diluent buffer. On the other line, sample was also serially diluted with buffer containing B19 antibodies. One hour later, the fixed cells were added to each well. The RHA inhibition titer was determined after 1 hour.

The result is shown in table 3.

TABLE 3

Screening of B19 virus by RHA (A) Screening of blood donors

|  | n | % |
|---|---|---|
| Screening by RHA (using PK7200) | 211,701 | 100.00 |
| Positive samples | 680 | 0.32 |
| RHA titer $2^6 \leq$ | 249 | 0.12 |
| Inhibition titer $2^1 \leq$ | 29 | 0.01 |
| PCR (+) | 13 | 0.01 |

(B) Comparison of RHA titer with PCR

| RHA titer $2^n$ | 12 | 11 | 10 | 9 | 8 | 7 | 6 | total |
|---|---|---|---|---|---|---|---|---|
| No. | 4 | 2 | 4 | 5 | 30 | 65 | 139 | 249 |
| PCR (+) | 4 | 2 | 2 | 2 | 1 | 0 | 2* | 13 |
| % positive | 100.0 | 100.0 | 50.0 | 40.0 | 3.3 | 0.0 | 1.4 | |

*anti-B19 virus antibody (+)

As shown in table 3(A), among 211,701 samples, 680 positive samples, including suspicious hemagglutination, were selected for a second confirmation test. 249 samples were more than $2^6$ of titer on RHA. Twenty-nine out of 249 samples were more than $2^1$ of titer on inhibition test. The non-specific rate of RHA by PK7200 was 0.32%.

Table 3(B) indicates that all samples with more than $2^{11}$ of RHA titer were also positive in PCR assay.

Considering the results of inhibition test and PCR, it is suggested that inhibition test as a second screening is desirable to confirm the results of the RHA test.

Example 5

Stability of RHA Reagents

We checked the titers of B19 viremic samples and negative samples by RHA at several time points. The test started 4 months after preparation of the RHA reagent. The result is shown in FIG. 1.

As shown in FIG. 1, the reagents for RHA were stable without the significant changes of titer for at least two months, from day 120 to day 191, after preparation.

The test may be a feasible method for detecting human parvovirus B19 because it is simple, sensitive, and applicable to automated hemagglutination machine that enable routine large-scale screening for the virus.

What is claimed is:

1. A method to detect human parvovirus B19, comprising the steps of:
   (1) bringing a blood sample selected from the group consisting of plasma and serum samples into contact with P-antigen positive O-group red blood cells in a medium comprising citrate-phosphate buffer or an acetate buffer of pH 5.6±0.6, to which a parvovirus B19 seronegative human AB serum has been added at a concentration of 0.1–2.0%, wherein said P-antigen positive O-group red blood cells have been fixed with 1% glutaraldehyde at 15 to 35° C. for 10 to 30 hours; and
   (2) determining whether or not hemagglutination occurs wherein the method is carried out by using an automated hemagglutination machine, wherein the occurrence of hemagglutination indicates the presence of human parvovirus B19 in the sample.

* * * * *